(12) United States Patent
Berthold et al.

(10) Patent No.: US 6,218,176 B1
(45) Date of Patent: Apr. 17, 2001

(54) METHOD AND APPARATUS FOR RAPID HYGIENE TESTING

(75) Inventors: Fritz Berthold, Eulerweg 3, D-75175, Pforzheim (DE); Peter E. Andreotti, Boca Raton, FL (US)

(73) Assignee: Fritz Berthold (DE)

( * ) Notice: Subject to any disclaimer, the term of this patent is extended or adjusted under 35 U.S.C. 154(b) by 0 days.

(21) Appl. No.: 09/367,039
(22) PCT Filed: Feb. 18, 1998
(86) PCT No.: PCT/IB98/00375
   § 371 Date: Oct. 15, 1999
   § 102(e) Date: Oct. 15, 1999
(87) PCT Pub. No.: WO98/37229
   PCT Pub. Date: Aug. 27, 1998

Related U.S. Application Data

(63) Continuation-in-part of application No. 08/904,832, filed on Aug. 1, 1997, now Pat. No. 5,905,029, which is a continuation-in-part of application No. 08/801,019, filed on Feb. 19, 1997, now abandoned.

(51) Int. Cl.⁷ ........................................ C12M 1/40
(52) U.S. Cl. ..................... 435/287.9; 435/288.1; 435/288.7; 435/810
(58) Field of Search .................. 435/8, 30, 31, 435/34, 287.2, 39, 287.4, 287.7, 287.6, 287.9, 288.1, 288.3, 288.4, 288.7, 304.1, 305.1, 305.2, 306.1, 307.1, 309.1, 810, 808; 422/52, 56, 58, 61, 82.08, 82.05; 600/572, 584

(56) References Cited

U.S. PATENT DOCUMENTS

| 5,159,197 | 10/1992 | Wannlund . |
| 5,278,075 | 1/1994 | Stone . |
| 5,905,029 | * 5/1999 | Andreotti ................................. 435/8 |
| 5,916,802 | * 6/1999 | Andreotti .......................... 435/287.7 |

FOREIGN PATENT DOCUMENTS

| 0 309 429 A2 | 3/1989 | (EP) . |
| 95/07457 A2 | 3/1995 | (WO) . |

OTHER PUBLICATIONS

International Search Report PCT/IB98/00375 dated May 6, 1998.

* cited by examiner

Primary Examiner—William H. Beisner
(74) Attorney, Agent, or Firm—Banner & Witcoff, Ltd.

(57) ABSTRACT

A rapid detection of ATP using dried luciferase/luciferin reagent. A liquid that may include an extraction reagent is applied to the testing surface, such as a counter top. A sampling device having a handle and an absorbent tip is wiped across the testing surface. The absorbent tip absorbs the sample. The sample is then placed in a counting tube. Luciferase/luciferin reagent is immobilized on the absorbent tip of the sampling device or in the bottom of a counting tube. In either case, the liquid rehydrates the luciferase/luciferin reagent allowing ATP present in the sample to react with the luciferase. Light produced by the reaction is measured with a luminometer.

5 Claims, 9 Drawing Sheets

METHOD AND APPARATUS FOR RAPID HYGIENE TESTING

This is a continuation-in-part of application Ser. No. 08/904,832, filed Aug. 1, 1997, now U.S. Pat. No. 5,905,029, which is a continuation-in-part of application Ser. No. 08/801,019, filed Feb. 19, 1997, now abandoned.

BACKGROUND OF INVENTION

This application relates to a device and a method for rapid hygiene testing by detecting ATP found in biomass on a test surface, such as a food preparation surface. From a sample taken from the surface, ATP is detected using a luciferase/luciferin bioluminescent reaction. The device and method of the present invention provides a quick, accurate determination of the cleanliness of surfaces.

It is important in many industries, such as food preparation, medicine, beverages, toiletries, and pharmaceuticals, to provide clean and sanitary surfaces. It is not enough to simply clean or sanitize a surface and assume it is free from microorganisms such as bacteria. Instead, a test must be performed to detect whether the surface is actually free of microorganisms. Thus, random areas of a surface, such as a food preparation surface, are tested for microorganisms to determine the general cleanliness of the surface.

One of the oldest methods to check for cleanliness involves culturing samples for bacteria. A test surface is chosen and wiped with a swab, and then the swab is smeared onto a culture medium. The medium is incubated and then checked for the presence of bacteria colonies grown in the medium. Over the years, various types of culture media have been developed along with numerous products based thereon. While the results of bacterial cultures are accurate, they are limited by the time that it takes to incubate the culture, usually in the order of days.

In response for a need to obtain results more quickly, other methods for detecting microorganisms were developed. Research soon focused on the detection of biomass on the test surface. Biomass includes living cells, dead cells, other biotic products such as blood, and food residue. It was discovered that biomass could be detected by detecting ATP, adenosine triphosphate, a chemical found in all living organisms.

The specific test for ATP involves the "firefly" reaction. The following is the reaction:

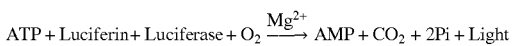

$$ATP + Luciferin + Luciferase + O_2 \xrightarrow{Mg^{2+}} AMP + CO_2 + 2Pi + Light$$

ATP, luciferin (D-luciferin cofactor), luciferase (enzyme) and oxygen are reacted in the presence of magnesium ion. Luciferin and luciferase are the same cofactor and enzyme present in fireflies that yields their namesake light. The products of the reaction are AMP (adenosine monophosphate), inorganic phosphate, carbon dioxide, and light (photons). The reaction, just as in fireflies, produces light. This light can be quantified and used to correlate to an amount of ATP. However, the amount of ATP does not necessarily relate directly to the number of microorganisms or bacterial cells or colonies. In fact, ATP may be from non-microbe biomass such as beef blood; thus the amount of ATP would not be related to microorganisms.

The lack of correlation may be due to the variation in ATP concentration within cells and the degradation of ATP in dead cells. ATP is found in all living cells, but the amount of ATP in cells can vary significantly. For example, prokaryotic cells have about one hundredth the amount of ATP as eukaryotic cells and different strains of bacteria will contain significantly different amounts of ATP. In addition, if a cell is growing or about to divide, it will contain more ATP than a dormant cell. Furthermore, cells that have just died contain ATP and even dead cells may contain ATP. In dead cells, any ATP present may degrade, often caused by a reaction between ATP and intracellular enzymes contained within the dead cells. All of these variables in ATP concentration mean that ATP testing is limited as a means to quantify the number of microorganisms or bacterial cells or colonies. However, ATP testing remains a method to qualitatively determine the presence of biomass, including microorganisms or bacteria.

Thus, the detection of ATP can be used to determine the presence of biomass, whether viable or nonviable. The ability to detect nonviable biomass is important, for example, in testing a surface for cleanliness because nonviable biomass (dead cells) such as food residue can provide a medium for living cells to grow.

Typically, the luciferase, luciferin, and magnesium ion are sold as a single combined reagent, not as individual reagents. The luciferase must be at the proper pH of 7.8 in order to be effective, usually achieved by employment of a buffer solution. If the proper pH is not mainined, the reaction will not work efficiently, and the results will be erroneous. However, luciferase is unstable while in solution, and will degrade, particularly at higher temperatures. Generally, at room temperature, the luciferase solution will remain effective for a period of hours whereas at near freezing temperatures, the luciferase solution will last for a period of days. In addition, luciferin in solution is light sensitive. Light causes the dissolved luciferin to degrade. Once the luciferin has degraded, no cofactor remains to unleash the bioluminescent reaction resulting in false negatives.

To prevent degradation, the luciferin and luciferase can be dried and protected from light. Methods for drying include, but are not limited to, freeze drying and lyophilization. The luciferase is more stable if kept out of solution. When ready to use, the dried luciferin and luciferase are dissolved in water containing an appropriate buffer to form an aqueous solution having the proper pH.

By mixing the luciferase/luciferin reagent with a sample taken from a test surface, extracellular ATP is immediately reacted and detected. However, intracellular ATP cannot be detected unless the ATP is first ectracted from within the cells. Typically, this is accomplished by mixing the sample with an extraction reagent (releasing reagent) which extracts the ATP from within the cells. The extracted ATP then can be mixed with the luciferase/luciferin reagent to produce the observable reaction. It is important that the extraction reagent chosen does not inactivate the luciferase/luciferin reagent. Nor should the extraction reagent be toxic if it is used on a food preparation surface, for example.

The luciferase/luciferin reagent cannot be stored with the extraction reagent as it will inactivate the luciferase and/or the luciferin over time. If either is inactivated, no light will be produced when combined with ATP. Therefore, the luciferase/luciferin reagent and extraction reagent must be stored separately until the time the test is conducted.

The bioluminescent reaction of ATP and luciferase/luciferin has traditionally been conducted using two basic types of systems: vial systems and all-in-one swab devices. A vial system uses a series of vials containing the reagents necessary to conduct the ATP tests. An all-in-one swab device provides all of the reagents and the swab in a self-contained apparatus.

In a vial system, for example, a first vial contains the extraction reagent, a second vial contains dried luciferase/luciferin reagent, and a third vial contains a buffered solution. At the time of the test, the luciferase/luciferin reagent is hydrated by adding the appropriately buffered solvent from the third vial to the vial containing the luciferase/luciferin reagent.

A sample is collected by wiping a pre-wetted swab across the testing surface. Typically, the swab is pre-wetted with saline. The swab containing the sample is placed in a test tube. Next, the proper amount of extraction reagent from the first vial is pipetted into the test tube containing the swab. After sufficient time has passed to ensure ATP extraction, the buffered solution containing hydrated luciferase/luciferin reagent is pipetted into the test tube and the luciferase is allowed to react with the ATP. The test tube is then placed into a luminometer where the amount of light produced by the reaction is measured. If more than one sample is taken, each sample is placed in its own test tube.

While vial systems produce correct results, there are deficiencies. One large problem is that the quantity of luciferase/luciferin solution prepared must be used within a short time period. If leftover solution is saved for later tests, the luciferase will degrade and ultimately become ineffective thus producing no reaction even in the presence of ATP. This problem is compounded by commercial producers of the luciferase/luciferin reagent that only sell the reagent in quantities that produce an amount of solution that is greater than that needed for individual tests. Furthermore, the dried luciferase/luciferin reagent is relatively costly. Thus the vial system results in waste of expensive reagents when only an individual test is required.

Another shortcoming of vial systems is that accurate pipetting and mixing of reagents is required. A pipette is used to transfer the reagents from vial to vial or vial to tube. While pipetting is accurate, it is laborious and time consuming. Further, if any of the vials or pipettes are not sterile, the biomass contained in them will produce a false positive for the presence of ATP.

The all-in-one swab devices apply the same reaction as the vial systems but keep all of the reagents and swab in a self-contained apparatus that fits into a luminometer. More specifically, the all-in-one devices typically involve a swab that is placed in a plastic tube containing several chambers. An advantage to this system is that a unit dose of each reagent is provided for one test, thus avoiding waste of reagents when only one test is required. However, a certain procedure must be followed using an all-in-one device to ensure that the reagents are combined at the appropriate times.

In a typical all-in-one device, a swab pre-wetted with a wetting solution is placed in a sealed tube until ready for use. The wetting solution may contain an extractant. The sealed tube prevents evaporation of the wetting solution. At the appropriate time, the device is opened, the pre-wetted swab is removed, and a sample is collected by wiping the swab along the testing surface. If present, the extractant will extract intracellular ATP from the sample collected on the swab. The swab is then placed back in the tube and the tube is resealed and ready for ATP reaction with the luciferase/luciferin reagents.

Dried luciferase/luciferin reagents are kept in a dry, stable state in the tube until mixed with a buffer solution. The luciferase/luciferin may be kept isolated from the wet swab by placing the luciferase/luciferin in a separate chamber in the tube which can be broken to expose the luciferase/luciferin to the buffer solution. Alternatively, the luciferase/luciferin may be in the form of a pellet that can be placed in a sealed container or can be stuck to the bottom of the tube.

A sealed chamber at one end of the tube contains the buffer solution. The tube is squeezed to break the barrier wall between the chamber and portion of the tube containing the swab, resulting in release of the buffer solution. The tip of the tube is then shaken to allow the luciferase/luciferin reagents to mix with the buffer solution, hydrate, and mix with the sample on the swab. The entire tube is then placed in a luminometer where the amount of light produced is measured.

While the all-in-one systems have overcome many of the problems of the vial systems, they have other shortcomings. For example, all-in-one systems are costly to manufacture since a complex tube arrangement is needed that is resealable and contains a breakable chamber to hold the buffer solution and possibly a second breakable chamber to hold the luciferase/luciferin.

Whatever system is used, the swabbing of the test surface should not itself contaminate the test surface. Thus, for example, the extracting agent used on the swab should not contain toxic chemicals that will leave toxic residues on the test surface.

Again, whatever system is used, the resulting tube containing the luciferase/luciferin and ATP is placed in a luminometer to read the light produced during the reaction. In the past, luminometers were designed with detectors aimed perpendicular to the axis of the sample tube so that when the sample is inserted in the luminometer's sample measurement chamber, the detector views the light produced by one side of the sample. Side-viewing luminometers are not a problem if ATP in solution is measured. Side-viewing detectors can be a problem if the sample being measured is absorbed onto a swab so that the light emitted is located on only one side of a swab, and that side is placed on the opposite side of the detector, then the amount of light reaching the detector will be less. Thus, the quantitative light measurement becomes dependent upon how the sample is placed in the luminometer.

More recently, a luminometer with a bottom-reading detector was developed which avoids the problems of side-viewing luminometers. A bottom-reading luminometer views the bottom of the sample tube and provides an accurate reading independent of the orientation of the sample, and whether the sample is in solution or absorbed onto a swab.

It is the object of the present invention to provide an accurate test for ATP with the convenience of the all-in-one system but with reduced unit cost. A further object is to provide an all-in-one system requiring a minimal amount of mixing and preparing of reagents. A further object of the present invention is to avoid waste of expensive reagents. A further object is to provide an accurate test that does not contaminate the tested surface. Finally, the invention will provide a system that can be used with either a side-viewing or a bottom-viewing detector.

SUMMARY OF THE INVENTION

The present invention is directed to rapid detection of ATP using dried and immobilized luciferase/luciferin reagent. The present invention provides an easier and cheaper means to test surfaces for cleanliness than either the vial method or the all-in-one method.

In accordance with the present invention, a solution that may include an extraction reagent is applied to the testing surface, such as a counter top. A sampling device having a handle and an absorbent tip is wiped across the testing surface. The absorbent tip absorbs the sample. The sample is then placed in a counting tube which is then placed in a luminometer.

In one embodiment of the present invention, luciferase/luciferin reagent is immobilized on an absorbent tip of a sampling device. In another embodiment, luciferase/luciferin reagent is immobilized in the bottom of a counting tube. In either case, ATP present in the sample reacts with the luciferase/luciferin and light is produced which is measured with a luminometer. In another embodiment, chlorhexidine (CDA) is used as the extraction reagent.

It was discovered that stable kinetics are obtained during reaction between ATP and the immobilized luciferase/luciferin when using the methods of the present invention. Immobilization is important to stabilize the luciferase/luciferin reagent and to provide a convenient means to combine a unit dose of the luciferase/luciferin reagent with the sample. In addition, it was discovered that immobilized luciferase/luciferin reagent provides stable light emissions not obtainable with liquid luciferase/luciferin solutions.

DETAILED DESCRIPTION OF THE INVENTION

Figure 1:
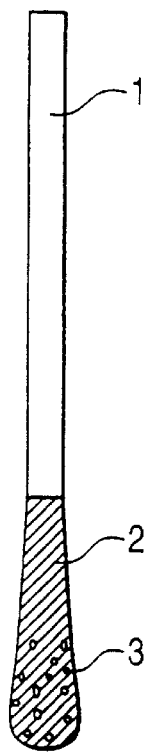
FIG. 1 depicts a sampling device of the present invention having a handle and an absorbent tip, and dried luciferase/luciferin immobilized on the tip.

As shown in FIG. 1, the present invention utilizes a sampling device having a handle 1 and a sterile absorbent tip 2. The sampling device is used to obtain a sample from the surface of a testing surface such as a counter top. By grasping the handle of the sampling device, the user can wipe (swab) a surface without contaminating the absorbent tip with, for instance, ATP from the user, which would result in false positives.

Suitable sampling devices include, but are not limited to, a natural or synthetic fibrous tipped swab such as a cotton or DACRON-tipped swab, or a piece of filter paper or sponge material attached to the tip of a handle. It is important that the sampling device be made from sterile materials to avoid contamination and false positive or negative results.

The sampling device can be used to detect ATP on a testing surface. In one method of using the sampling device, at least one, preferably one to three, drops of a suitable solution (approximately 125 $\mu$l) are applied to the test surface. The solution is added in an amount sufficient to load the absorbent tip but not leave significant excess solution on the test surface. The solution may or may not contain an extraction reagent.

The absorbent tip of a sampling device is then wiped across the solution on the test surface to obtain a sample and, if an extraction reagent is used, to extract any intracellular ATP from the sample. The sampling device is then placed in a counting tube.

Dried luciferase/luciferin is either immobilized on the absorbent tip of the sampling device or in the counting tube. In either case, the sample absorbed onto the absorbent tip rehydrates the dried luciferase/luciferin allowing the luciferase to react with any ATP present in the sample. The reaction is allowed to equilibrate, typically, about 30–90 seconds. The counting tube is then inserted into the luminometer to measure the amount of light produced by the reaction which can be correlated to an amount of ATP.

In one embodiment of the present invention, the absorbent tip of the sampling device has immobilized luciferase/luciferin as shown in FIG. 1 Luciferase/luciferin reagent is immobilized on the absorbent tip of the sampling device, for example, by absorbing concentrated luciferase/luciferin reagent solution onto the absorbent tip of the sampling device and then drying. Alternatively, the enzyme and cofactor are bonded covalently to the absorbent tip in such a way to maintain the chemical activity of the enzyme. An advantage of covalently-bonded absorbent tips is that the strong covalent bond keeps all of the luciferase/luciferin reagent on the absorbent tip and off of the testing surface, thus maintaining the cleanliness of a test surface.

Figure 2:
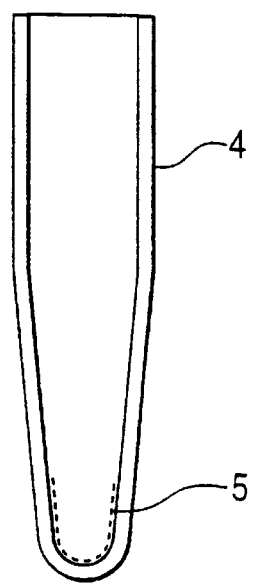
FIG. 2 depicts a counting tube of the present invention having immobilized, dry luciferase/luciferin on the bottom wall of the tube.

Another embodiment of luciferase/luciferin rapid-hygiene testing is a luciferase/luciferin enriched counting tube. Instead of luciferase/luciferin being immobilized on the absorbent tip of the sampling device, the reagent is immobilized in a counting tube. FIG. 2 shows immobilized luciferase/luciferin on the inside bottom wall or surface 5 of a counting tube 4. In this embodiment the luciferase/luciferin reagent never contacts the test surface thus avoiding contamination of the test surface.

An enriched luciferase/luciferin counting tube is made by first placing luciferase/luciferin reagent solution into the bottom of a counting tube and then drying to remove the solvent and immobilize the luciferase/luciferin reagent. Concentrated luciferase/luciferin reagent solution is preferred because a smaller amount of solvent is used and drying takes less time.

Both the sampling device and luciferase/luciferin enriched tubes of the present invention provide a per unit dosage. Thus one sampling device is used at a time and waste that often accompanies the vial methods, for example, is avoided. The device of the present invention has a cheaper per unit cost and is easier to manufacture than the complex all-in-one systems.

The sampling device may be a standard swab which is about 15 cm long. The majority of luminometers can only accommodate a swab height between about 5 and 7.5 cm, therefore the length of the swab handle needs to be shortened accordingly. Although standard swabs that are shortened by the user can be used in the present invention, it is not preferred since there is a risk that the part of the swab which is cut off might fall into food preparation surface and get lost. Preferably therefore, a swab is produced and provided to the user that is approximately 9.5 to 12 cm long, more preferably about 10 cm long. This length allows for good handling but is not too long for insertion in most luminometers.

The tube must be shorter than the swab so that the swab handle can be gripped and rotated manually while the swab tip is in contact with the bottom of the tube. On the other hand, the tube should not be shorter than necessary to allow convenient handling and reduce the risk of getting lost in the food manufacturing site. The tube height is typically between about 5 and 8.5 cm in height, preferably about 7.5 cm and thus about 2.5 cm shorter than the preferred swab length. The outside diameter of the tube is typically about 10 to 12 mm, preferably about 12 mm.

Although any typical counting tube may be used, it was determined that a standard tube with a 12 mm outside diameter and a round bottom requires a zigzag motion to bring the swab tip in contact with all the immobilized regions at the tube bottom and the results are not easily reproducible. It was discovered that the best performance is obtained when the tube bottom and the swab tip are dimensioned so that the entire reagent-covered area at the tube bottom is in contact with the swab tip simultaneously.

Figure 8:
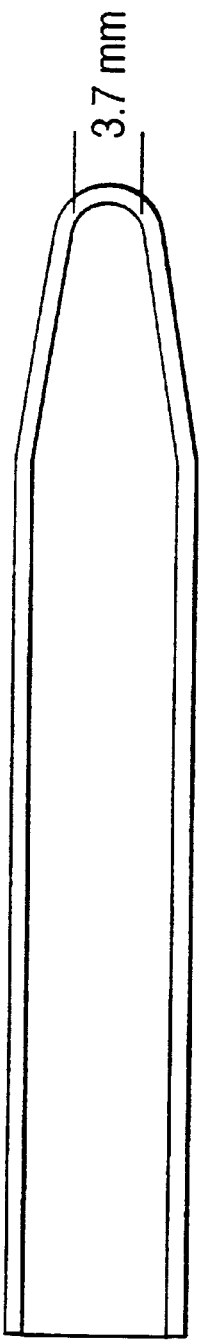
FIG. 8 depicts a conventional counting tube.
Figure 9:
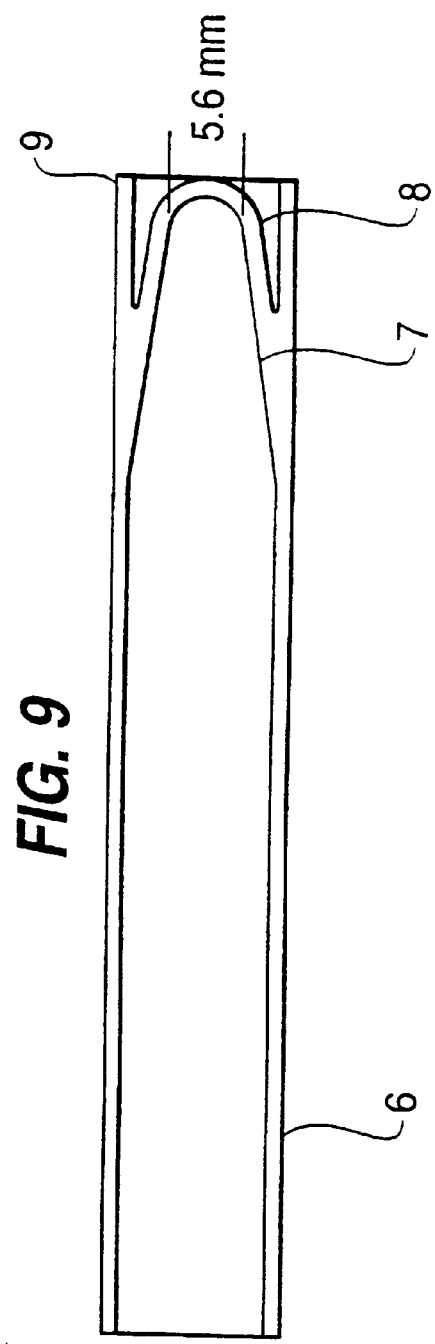
FIG. 9 depicts a counting tube in accordance with the present invention.

As indicated in FIG. 8, conventional commercially available 12 mm outside diameter conical bottom tubes have a hemispherical bottom with inside diameter of 3.7 mm. When a swab is wetted with CDA to absorb the test sample, the swab head expands, typically to a diameter of about 5.6 mm. Thus the wet swab has to be squeezed down into the bottom of the 3.7 mm inside diameter tube and then twisted to solubilize the dried luciferase/luciferin in the swab tip. This creates variable readings. Although such conventional tubes are suitable for the present invention, it is preferred that the upper part 6 of the tube is cylindrical, and the bottom 20 mm or so 7 is conical so that the bottom point 8 has an inside diameter between about 4 and 6 mm, preferably about 5.6 mm inside diameter, as shown in FIG. 9. This provides the swab with a snug but not too tight fit at the bottom and provides optimum contact between the (wet) swab lip and the immobilized reagents. A simple rotation about the swab au is sufficient to obtain mixing. FIG. 9 also shows an optional skirt 9 which allows the tube to stand on end.

It was also discovered that higher counts (RLU/s) and better reproducibility are obtained with the bigger ID tubes thus less luciferase/luciferin solution is needed to make the tubes resulting in lower cost.

Any suitable method may be used to prepare the luciferase/luciferin reagent for use on the absorbent tip of the sampling device or the coated tube of the present invention. In a preferred method, a stock luciferase solution is prepared by diluting luciferase to a concentration of 0.02 to 0.04, preferably 0.03, mg/mi in HEPES buffer of pH 7 to 8, preferably pH 7.8, containing 4.766 g/liter HEPES, 1.22 g/liter magnesium sulfate, 0.744 g/liter EDTA, and 2.5 to 5, preferably about 5% BSA. The stock luciferase solution is mixed with an equal volume of stock luciferin solution containing 1 to 3, preferably 2, mg/ml of D-luciferin dissolved in HEPES buffer pH 7.8. A volume of 10–20 μl (preferably 15 μl) of the luciferase/luciferin working solution is added and then dried in the absorbent tip of the sampling device or 10 to 50 μl (preferably 25 μl) is dried in bottom of counting tubes. Alternatively, the concentrated working solution is diluted ten-fold in HEPES buffer and then approximately 125–175 μl (preferably 150 μl) of the diluted working solution is dried in the absorbent tip of the sampling device by dipping the tip in the diluted working solution and then drying it, or approximately 125–175 μl (preferably 150 μl) of the diluted working solution is dried in the bottom of counting tubes.

In another method, D-luciferin is dissolved in a sterile, pH 7.8, HEPES (N-2-hydroxyethylpiperazine-N-2-ethanesulfonic acid) buffer at 0.73 mg/ml. Luciferase is dissolved in sterile 0.5 M Tris-succinate buffer pH 7.5 with 1% BSA (bovine serum albumin) to create a solution with a concentration of 1.0 mg/ml. Then 102.5 ml of D-luciferin solution, 23.75 ml of luciferase solution, and 41.25 ml of 3% BSA dissolved in water are combined to form the luciferase/luciferin solution. HEPES has a $pK_a$ of 7.55 at 20° C. and meets Good's criteria for a zwitterionic buffer.

If a treated absorbent tip is being used, the concentrated or diluted lucifase/luciferin reagent solution is absorbed onto the absorbent tip of the sampling device. The tip may be dipped into the solution, or about 125 to 175 μl of solution, having 100 to 200 ng, preferably 150 ng, of luciferase and 5 to 10 μg, preferably 7.5 μg, of luciferin, may be added to the tip. The amount of luciferase/luciferin reagent is the quantity that maximizes the amount of light produced by the luciferase/luciferin reaction while also maintaining a stable reaction that will be measurable for as long as possible.

If the enriched tube is being used, the luciferase/luciferin reagent is applied and immobilized to line the bottom of the tube. For instance 10 to 50 μl, preferably 25 μl, volume of the concentrated luciferase/luciferin reagent solution, having 100 to 1,000 ng, preferably 375 ng, of luciferase and 5 to 75 μg, preferably 25 μg, of luciferin, is placed in the bottom of the tube and then dried to effect immobilization. The amount of luciferase/luciferin reagent is the quantity that maximizes the amount of light produced by the luciferase/luciferin reaction while also maintaining a stable reaction that will be measurable for as long an amount of time as possible.

Drying of the luciferase/luciferin reagent on the absorbent tip of the sampling device or in the enriched tube may be by any suitable means such as drying in a refrigerator at 4–8° C. for 12 to 72 hours, freeze drying or lyophilization which is essentially evaporation of the liquid under vacuum at freezing temperature (−40° C.). Preferably no heat is used to dry the solution since heat can degrade the luciferase/luciferin reagent. Thus, methods involving dry, cold environments are preferred. Freeze drying method is used to make pellets or powder of the all-in-one of a vial systems. However, such pellets or powder would fall or fly out of uncapped tubes. Such systems do not recognize the use of luciferase/luciferin reagent immobilized onto the tube itself.

Refrigeration drying can be used and causes the luciferase/luciferin solution to dry as a film and adhere on the bottom of the tube. Although it can be used in the present invention, refrigeration drying is not preferred because it is inefficient and sometimes the film does not dry completely, i.e. the film may remain somewhat sticky due to the protein (BSA and luciferase) which are hygroscopic and absorb water molecules. When this happens, the dried luciferase/luciferin on the bottom of the tube is not stable and its activity decays. It was discovered that if the luciferase/luciferin solution is first dried in a refrigerator for (24–72 hours) to immobilize the film layer of luciferase/luciferin/BSA in/on the bottom of the tube, and then freeze-dried in a lyophilizer for a short period of time (30–120 minutes) to finish drying, the film layer produced is immobilized and stable.

Figure 10:
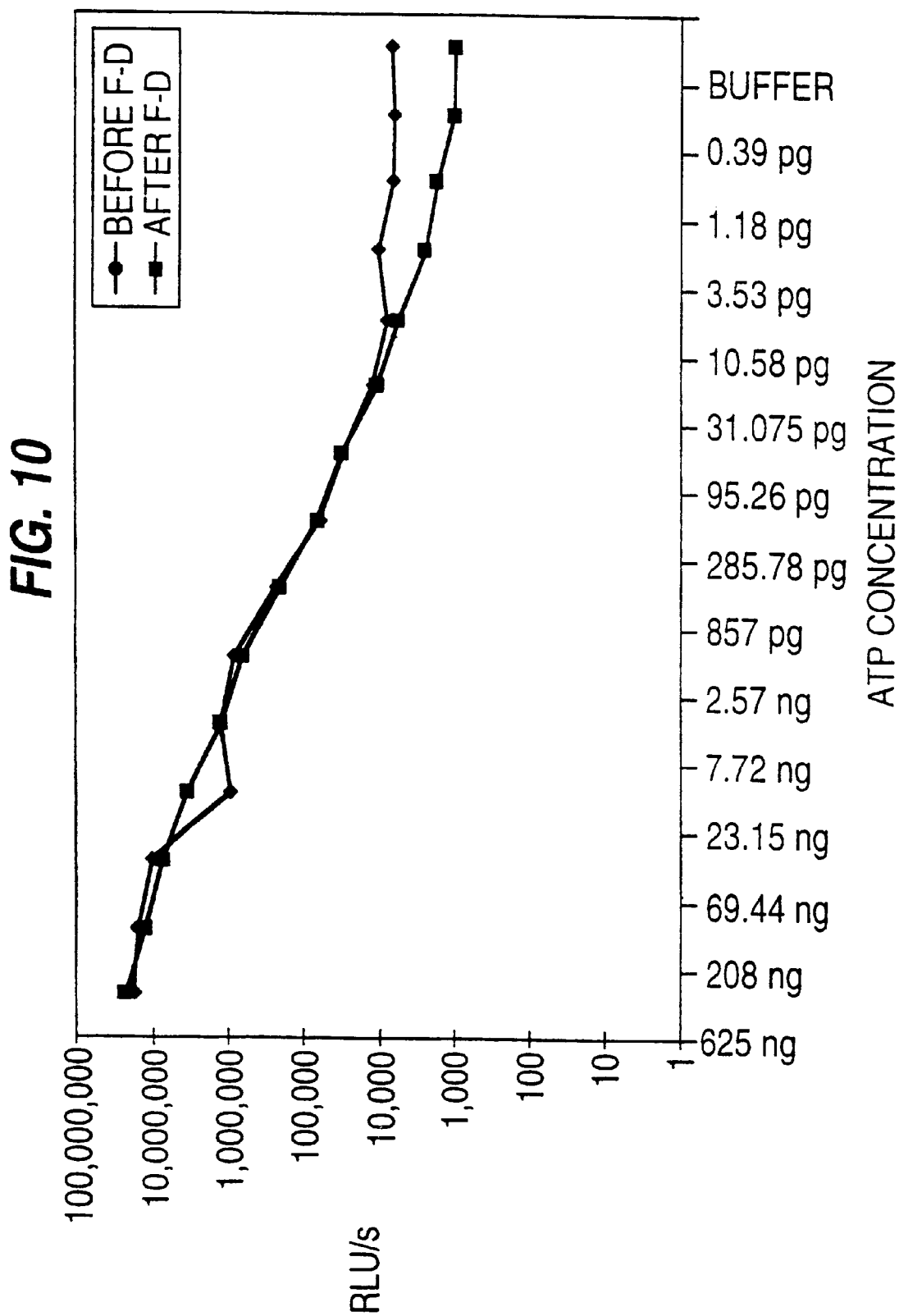
FIG. 10 depicts ATP standard curve with tubes prepared Dec. 8, 1997 before and after freeze-drying (30' inc.).
Figure 11:
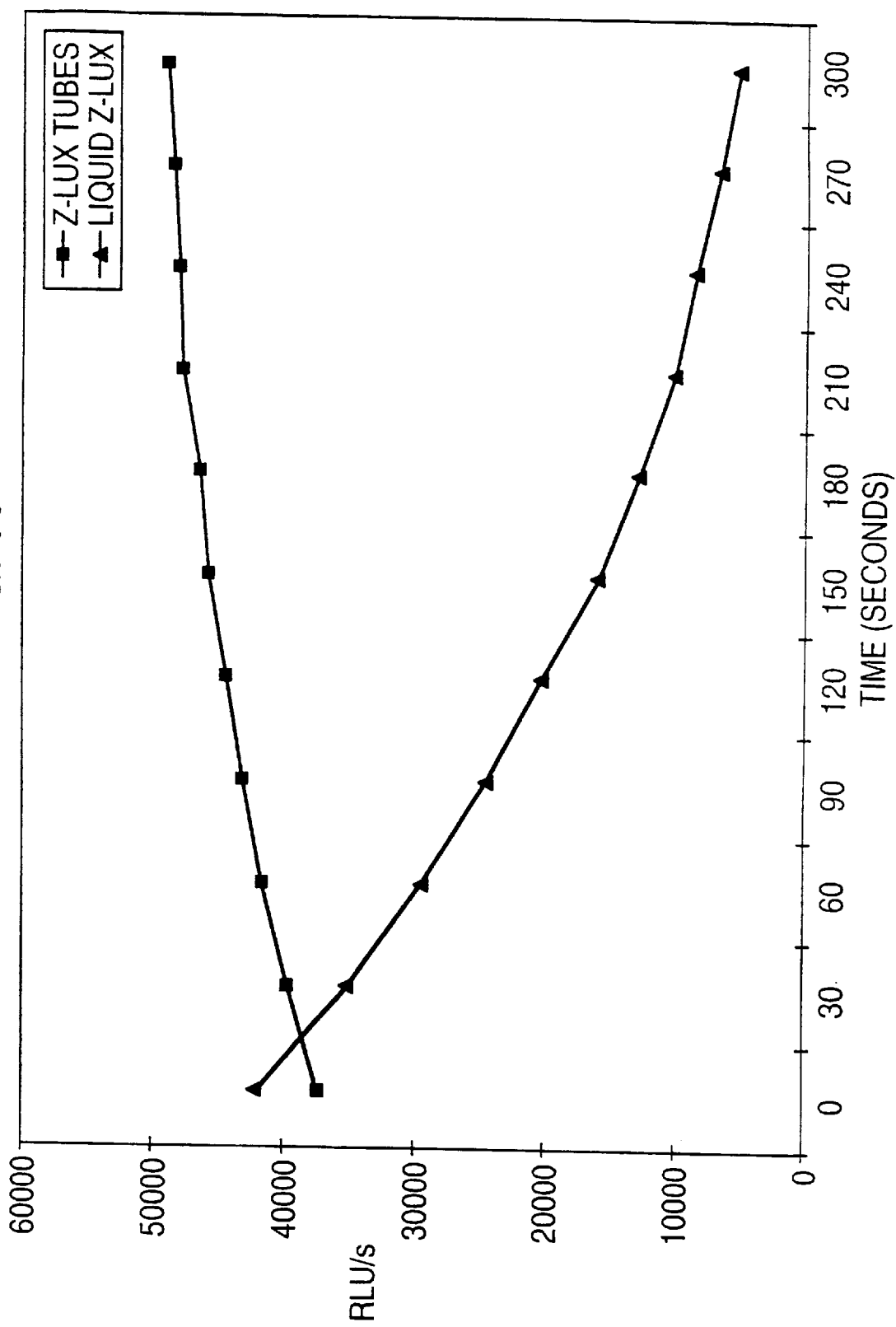
FIG. 11 compares samples of *E. coli* extracted with CDA and placed in either liquid luciferase/luciferin or luciferase/luciferin immobilized on the bottom wall of a counting tube (*E. coli* extracted with Z-X and counted with Z-lux tubes or Z-lux liquid).

FIG. 10 shows improvement of counting tubes with and without freeze drying for 30 minutes after refrigeration drying of 25 μl of luciferase/luciferin in the bottom of the tube for 72 hours. Counting tube activity is determined by measuring the RLU/s produced when dilutions (1:3) of an ATP standard solution in 0.1 M HEPES buffer pH 7.8 are added to replicate counting tubes and the tubes are then measured in a luminometer. FIG. 10 shows that lower ATP concentrations in the range of 1.18–10.58 pg can be measured over the buffer background (no ATP) after but not before freeze-drying the tubes. This procedure allows for the use of uncapped tubes.

The solution applied to the test surface is typically provided in a dropper bottle to allow easy storage and application. A dropper bottle also releases the solution accurately enough to perform the test. The solution may be any suitable solution to allow absorption of a sample onto the absorbent tip of a sampling device such as water, saline, or pH 7.8 HEPES buffer solution. The solution may also contain an extraction reagent to obtain intracellular ATP.

The extraction reagent may be any suitable reagent that can release ATP in a sample. Suitable extractants include cationic and non-ionic detergents, and surfactants such as TRITON solution. The amount of extracting agent is the quantity to maximize the amount of light produced by the luciferase/luciferin reaction while maintaining a stable reaction that will be measurable for as long an amount of time as possible.

The preferred extractant is chlorhexadine diacetate (CDA) solution. It was discovered that CDA, against expectations that it would inactivate the luciferase/luciferin reagent, is in fact a very effective extractant for use with the immobilized luciferase/luciferin systems of the present invention. Furthermore, it is nontoxic and will not contaminate the test surface. CDA is, in fact, a common ingredient of dental mouthwash. CDA may be prepared by dissolving 0.05 g of chlorhexadine diacetate in 50 ml of water, and then adding more water to reach a 1:2–1:8 volumetric ratio. CDA can also be prepared in pH 7.8 buffer containing HEPES (0.477 g/100 ml of water) without $Mg^{++}$ in the buffer.

The luminometer may be a side-viewing or bottom-detecting luminometer. Although side-viewing are more prevalent, the preferred type of luminometer is a bottom-detecting luminometer. The advantage of using a luminometer with a bottom seeing detector is that it will obtain an accurate reading regardless of how the swab is rotated in the luminometer's sample tube.

The counting tube should be sized so that it can be placed directly into a luminometer and should be made of a material that absorbs as little light as possible in the frequency that the ATP/luciferase/luciferin reaction produces (mostly yellow and green) in order to assure an accurate reading. Examples of suitable materials are glass, polystyrene, polypropylene, and polyethylene. Preferably, the tube is made of polystyrene or polypropylene.

The present invention is also directed to a kit for rapid hygiene testing. The kit can be modified for the particular user. A typical kit may contain:

10 vacuum sealed opaque bags containing 10 dried luciferase/luciferin counting tubes per bag.
2 dropper bottles containing 15–20 ml of CDA solution each.
10 plastic vials containing 10 sterile, plain Dacron swabs (96 mm) each.
10 biohazard disposable bags.
1 instructional manual.

In contrast to the all-in-one systems which are closed systems in which the swab and reagents are in a closed plastic device, the present system is "open" in that the swab and reagents are separate and the luciferase/luciferin counting tubes do not need a cap. It is manufactured and uncapped in the vacuum sealed opaque bag. This reduces manufacturing cost and also eliminates a small plastic cap piece which could fall-off and get lost in the food processing environment where the testing is taking place. The "open" system of the present invention requires luciferase/luciferin in the counting tube that is not just dried, but also immobilized in/on the bottom of the tube. A single, unit dose of dried luciferin-luciferase which is dried and immobilized in the bottom of the tube that is put into the luminometer.

Prior all-in-one (and vial) systems have freeze-dried "pellets" (ca 3–4 mm) or powder containing the luciferin, luciferase and buffer. Since the tubes of the present invention are uncapped, pellets or powder would fall or fly out of the tube in the packaging or when the tubes are being handled. Hence, the need to immobilize both the luciferase enzyme and luciferin in/on the bottom of the tubes.

EXAMPLES

Example 1

Figure 3:
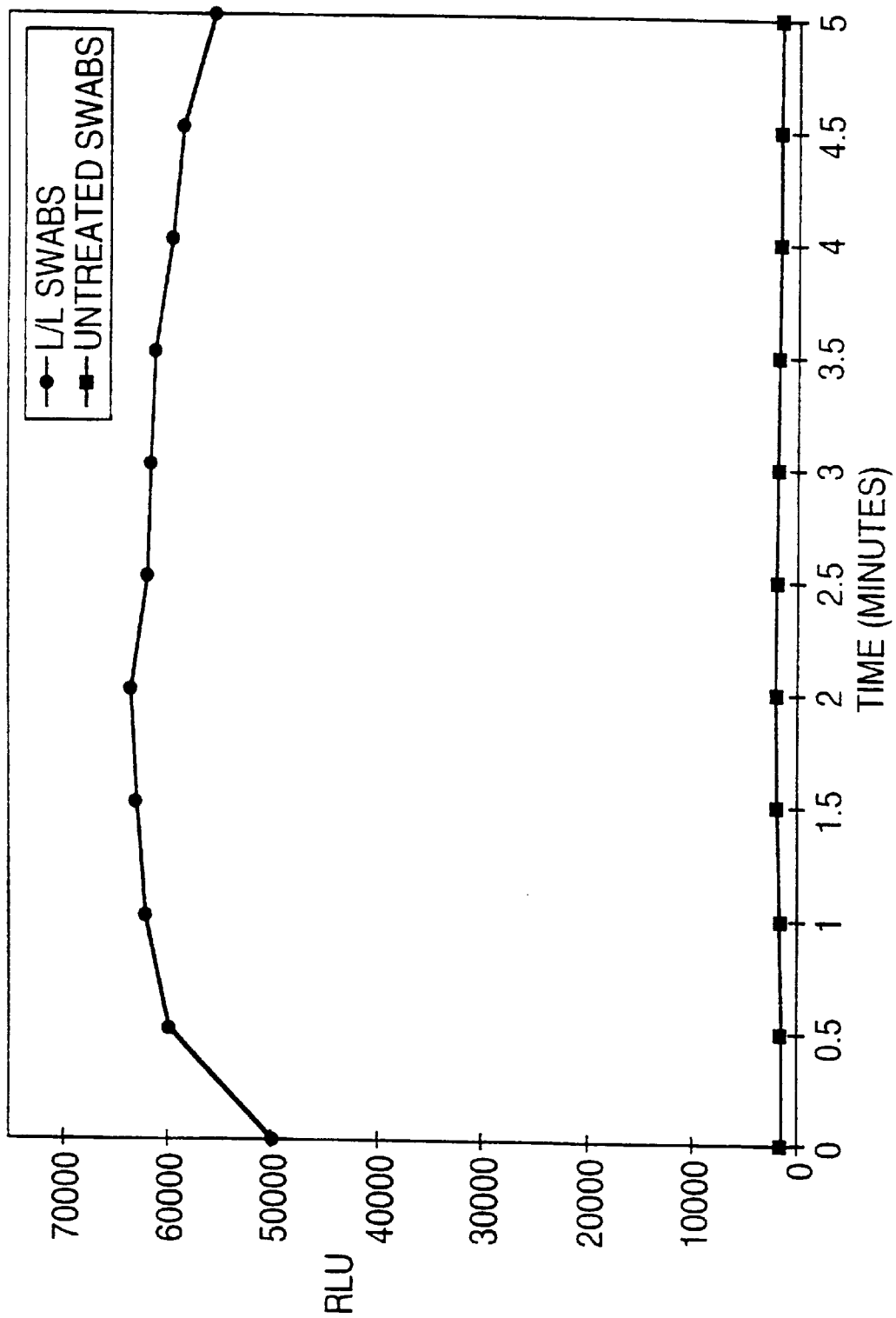
FIG. 3 depicts ATP measurement of bacterial samples with CDA extractant, luciferase/luciferin swabs and untreated swabs.

20 μl of a bacterial culture was placed on a sterilized surface. Next, two drops of extractant chlorhexadine diacetate (CDA) were added. Then, a luciferase/luciferin-treated swab was rubbed on the test surface and the extractant was absorbed. In addition, a control swab that contained no luciferase/luciferin reagent was tested under identical conditions. Each swab was placed in a counting tube and inserted into a luminometer where the amount of light produced was measured for five seconds at 30 second intervals for five minutes. The results are shown in FIG. 3. Each point represents the mean of three repeated tests. The results demonstrate the efficacy of the invention for detecting the ATP present in a bacterial sample. ATP was measurable with the luciferase/luciferin treated swab, but not the control untreated swab. The amount of light produced by the reaction is relatively stable over the five minute period.

Example 2

Figure 4:
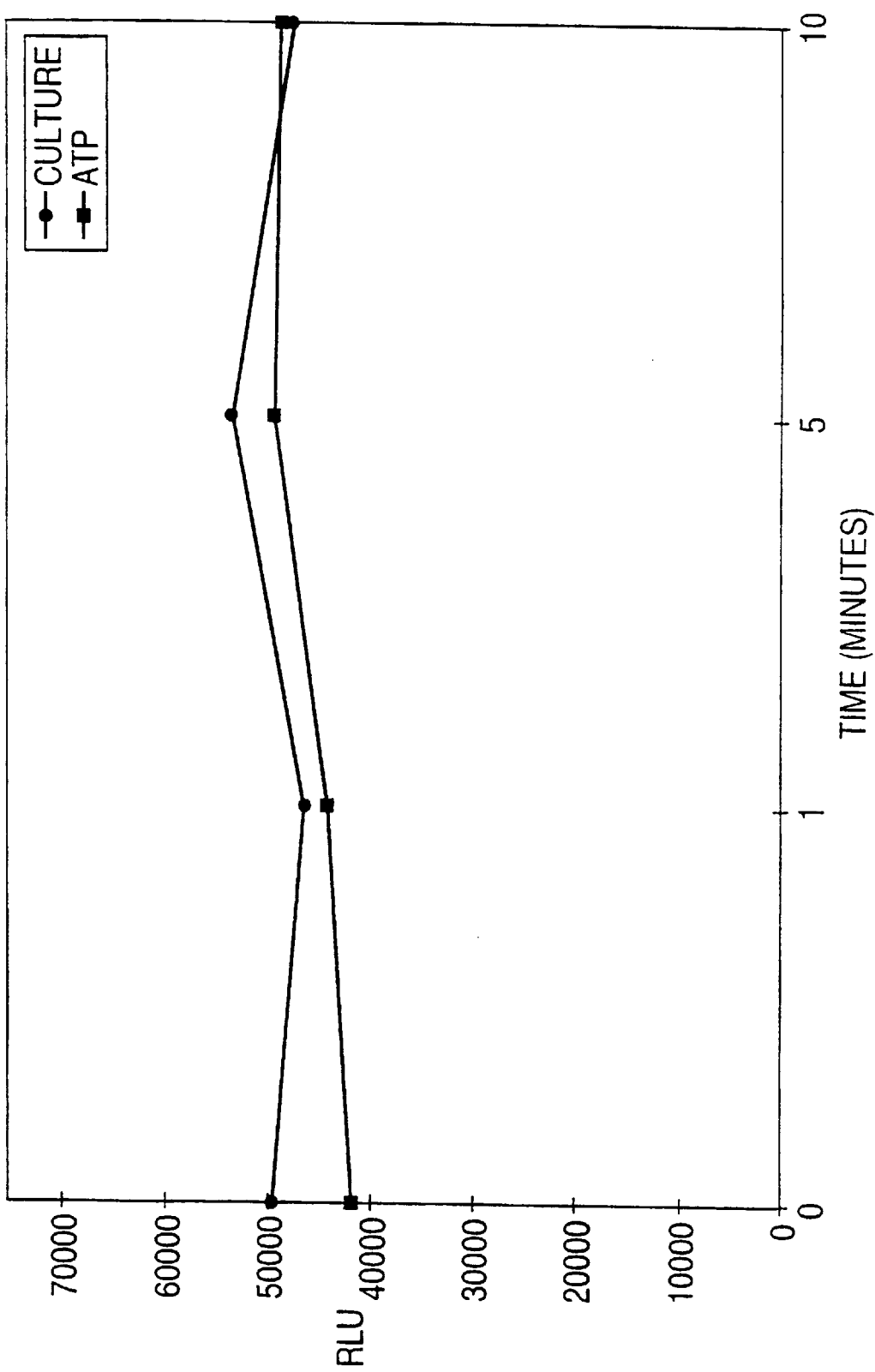
FIG. 4 depicts ATP measurement of bacterial sample and ATP with CDA extractant and luciferase/luciferin swabs.

Two types of samples were tested for the presence of ATP. The first sample was a bacterial culture. The second sample was an ATP solution. Four 20 μl aliquots of each sample were placed on a sterile surface. Next, two drops of CDA extraction reagent were added to each of the aliquots and then the aliquots were allowed to sit for a period of time, depending on the sample; one aliquot of each sample was allowed to sit for 0 minutes, another for 1 minute, another for 5 minutes, and a final for 10 minutes. Next, after the designated amount of time, a luciferase/luciferin reagent-containing swab was rubbed on the surface of the sample and the extraction reagent was absorbed into the swab. Next, the swab was placed in a counting tube which was then inserted into a luminometer to measure any light produced. Each experiment was repeated three times and the mean of the results were plotted. The results are shown in FIG. 4 and demonstrate that the amount of ATP present remains stable in the presence of the extraction reagent for a period of at least ten minutes.

Example 3

Two experiments were performed with the same bacterial sample and CDA extraction reagent as Example 1. The first experiment was performed with a solution of the luciferase/luciferin reagent used to prepare swabs. The second experiment was performed using a luciferase/luciferin treated swab.

Figure 5:
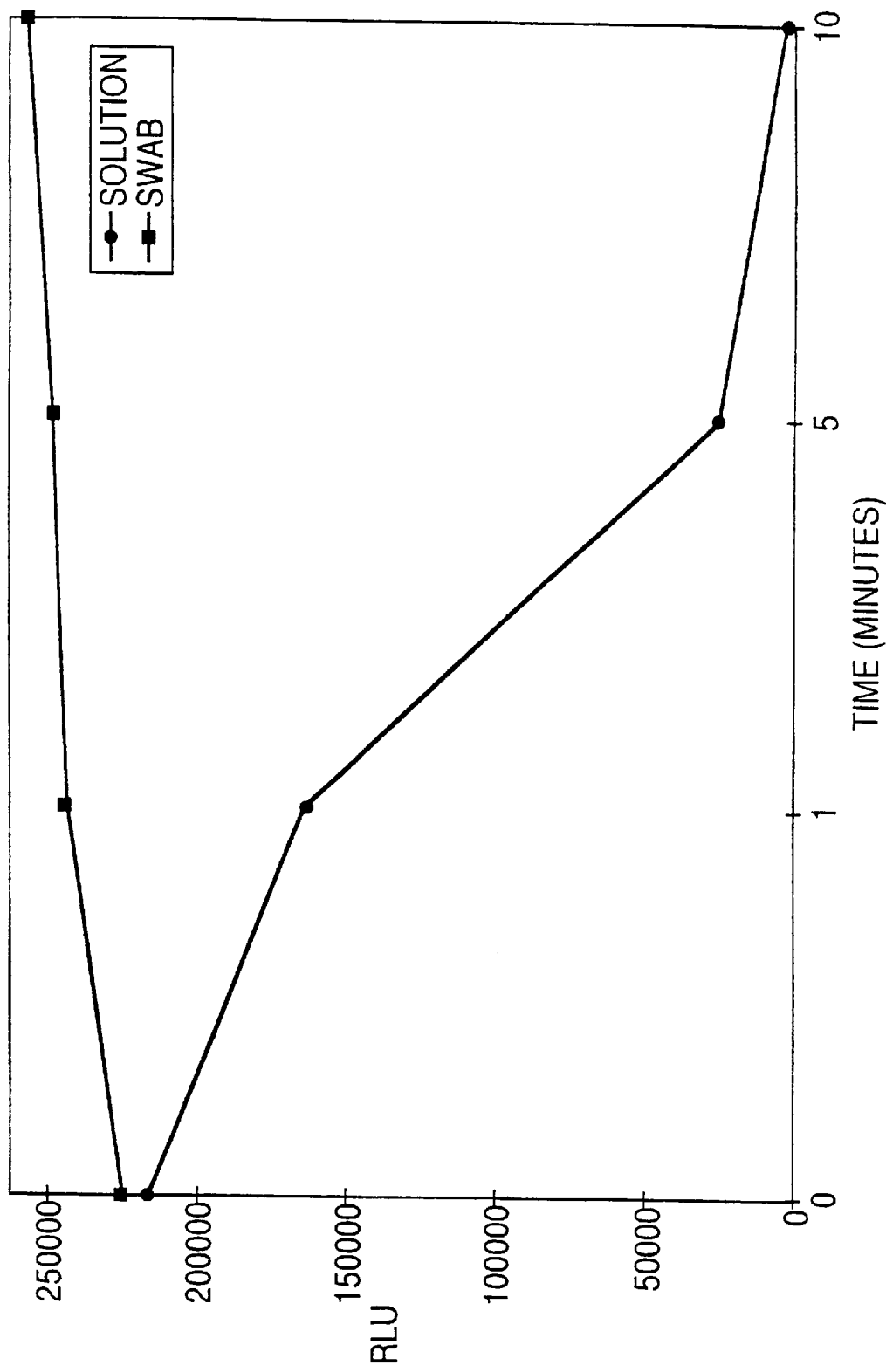
FIG. 5 depicts inactivation of luciferase/luciferin solution by CDA compared to the stability of luciferase/luciferin swab—results with bacterial culture sample.

In the first experiment, four separate 125 μl aliquots of the extractant were mixed with 50 μl aliquots of the luciferase/luciferin solution in luminometer counting tubes. Each of the four mixtures was then allowed to sit for a period of time. The first sat for 0 minutes; the second sat for 1 minute; the third sat for 5 minutes; and the fourth sat for 10 minutes. After the designated period of time, 20 μl of bacterial culture was added to the tube. The tube was then placed in a luminometer and the amount of light produced was measured. Results for the first experiment are depicted in FIG. 5 by the "Solution" curve and illustrate the originally expected but undesirable result that mixing of the extraction and luciferase/luciferin reagents before adding the sample causes a loss in efficacy and subsequent complete inability to measure ATP in the sample within minutes. These results may be attributable to either the inactivation of luciferase/luciferin by the CDA or, conversely, inactivation of the ATP extraction capability of the CDA by the luciferase/luciferin.

The second experiment shown in FIG. 5 was performed in the same manner as described in Example 1 using a luciferase/luciferin-treated swab. Measurements were made at 0, 1, 5, and 10 minutes after adding 2 drops of CDA to a 20 μl sample of bacterial culture and then absorbing the extracted sample into the tip of the swab. Results for the second experiment are depicted with the "Swab" curve and illustrate, again, the efficacy for detecting bacterial ATP with the invention, and stability of light produced over a ten-minute period using the invention.

Example 4

Figure 6:
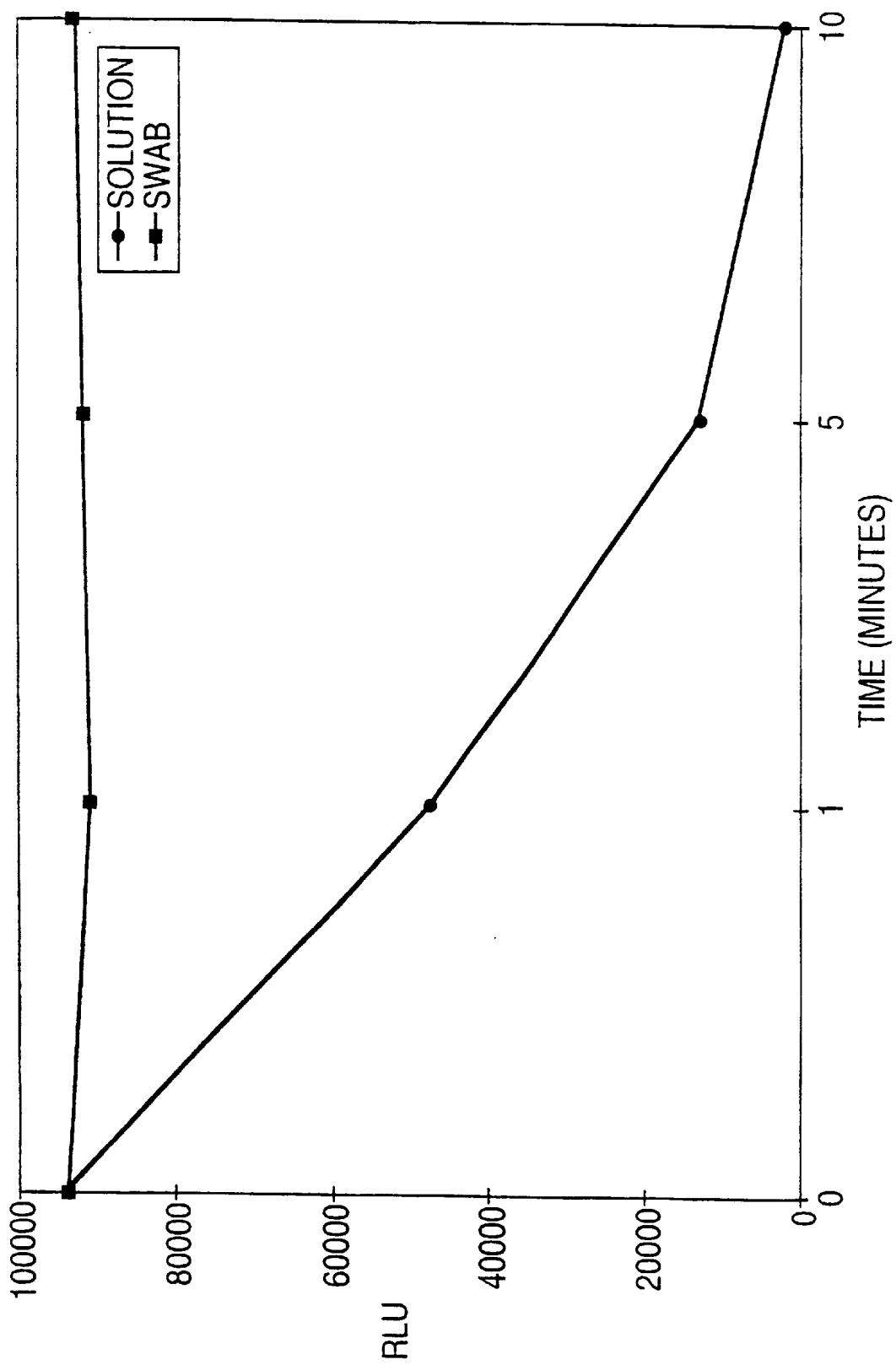
FIG. 6 depicts inactivation of luciferase/luciferin solution by CDA compared to the stability of luciferase/luciferin swab—results with ATP solution sample.

Experiments were performed in the same manner as the experiments in Example 3 except 20 μl of an ATP solution was used instead of a bacterial culture sample. As can be seen in FIG. 6, a decrease in measured light output was again observed for the "Solution" experiment using the ATP solution which does not require extraction of ATP from inside of cells for the light-producing reaction to proceed. This result indicates that the loss in efficacy and subsequent complete inability to measure ATP in the "Solution" experiments in FIGS. 5 and 6 is due to inactivation of luciferase/luciferin by the CDA, which does not occur with the invention. The "Swab" curve results in FIG. 6 again illustrate the efficacy and stability for measuring ATP with the invention.

Example 5

Figure 7:
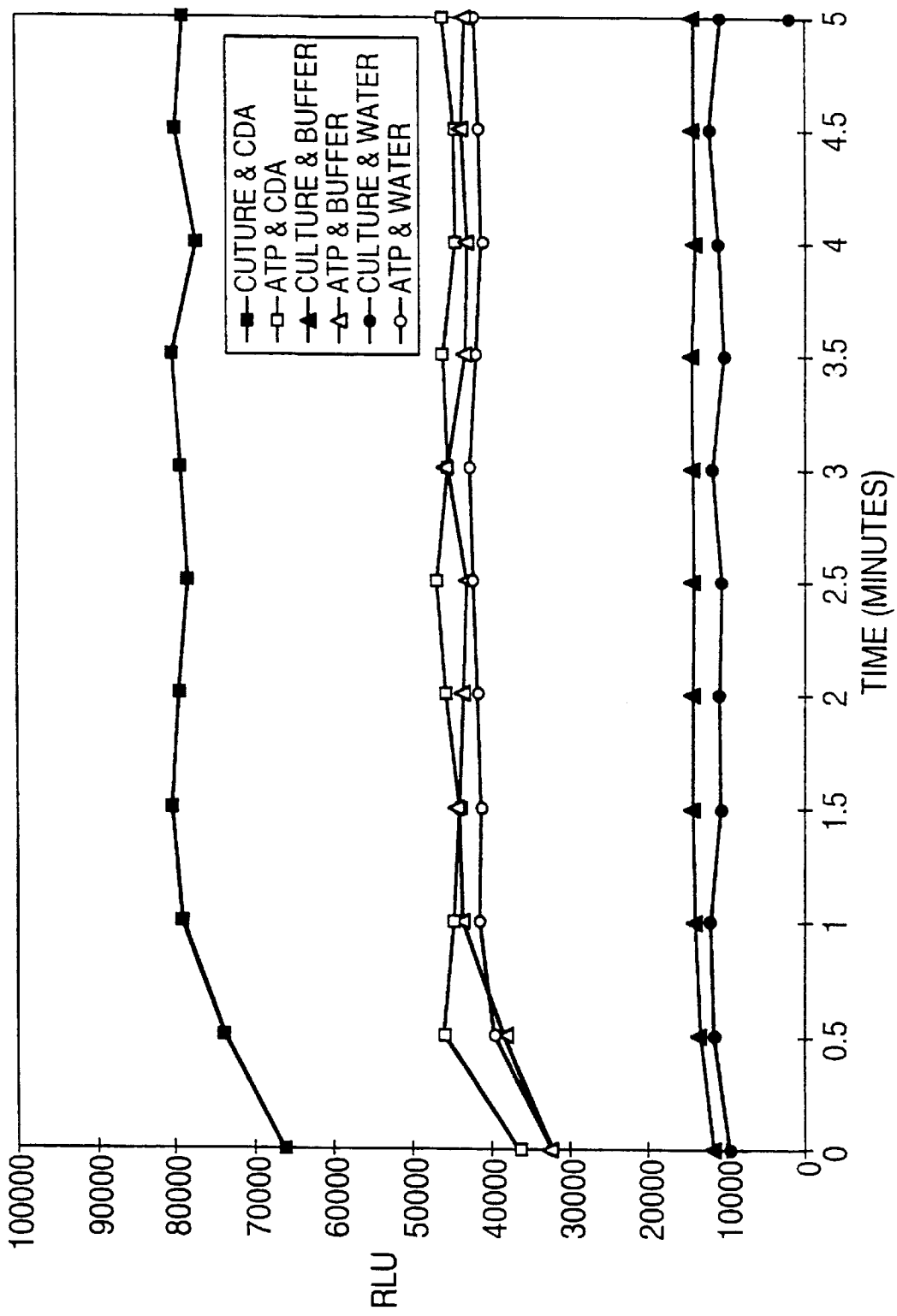
FIG. 7 depicts measurement of bacterial culture or ATP samples with different solutions, untreated swabs, and dried luciferase/luciferin tubes.

Comparisons were made between ATP in a bacterial culture and ATP from an ATP solution with three liquids: CDA, buffer, and water. Three separate 20 μl aliquots of bacterial culture sample and three separate 20 μl aliquots of ATP solution were put on a sterile surface. Next, three drops of CDA were added to one of the bacterial sample aliquots and three drops of CDA were added to the first ATP sample aliquot. At the same time, three drops of pH 7.8 HEPES buffer were added to the second bacterial sample aliquot and three drops of pH 7.8 HEPES buffer were added to the second ATP sample aliquot. At the same time, three drops of water were added to the third bacterial sample aliquot and three drops of water were added to the second ATP sample aliquot. Next each treated sample was rubbed with the absorbent tip of a sampling device so that the sample and the liquid were absorbed into the tip. Next, the sampling device was put into an immobilized luciferase/luciferin reagent tube. The immobilized reagent was mixed with the liquid that had been absorbed in the absorbent tip to dissolve the luciferase/luciferin reagent. The tube containing the sampling device was then placed into a luminometer. The amount of light produced in each tube was measure at half-minute intervals through a period of 0 minutes through 5 minutes. The results are shown in FIG. 7.

Each reaction combination was plotted with its own points: black square for culture and CDA, open square for ATP solution and CDA, black triangle for culture and buffer, open triangle for ATP solution and buffer, black circle for culture and water, open circle for ATP solution and water.

Light was produced with all of the ATP solution samples regardless of whether CDA, buffer, or water was used which indicates that extracellular ATP can be measured using any of CDA, buffer, or water. However, only CDA produced light with the culture sample which shows that intracellular ATP was only detected using CDA The culture samples with buffer or water did not produce light thus indicating that intracellular ATP cannot be measured with the buffer or water.

In addition, after an initial equilibrium period (0–1 minute), the plots all were flat. The flatness in the line indicates that a constant amount of light is being produced throughout the duration of the experiment.

Example 6

Dropper bottles were prepared with 0.1, 0.05, 0.025, and 0.0125% CDA solutions. 64 separate 20 μl aliquots of an *E. coli* culture were pipetted into a number of petri dishes. Then, 1, 2, 3, or 4, drops of each CDA concentration were added to a separate *E. coli* aliquot After an extraction time of 0, 30, 60, or 90 seconds, a plain DACRON swab was used to obtain a sample by wiping the culture plus CDA solution over an approximately 2×2 cm$^2$ area. Each swab was then placed in a round bottom polystyrene counting tube containing 20 μl of luciferase/luciferin reagent and rotated to absorb the liquid luciferase/luciferin into the swab tip. RLU were then measured every 30 seconds for 210 seconds. Liquid luciferase/luciferin reagent was used to ensure a constant volume.

Two to three drops of 0.05% to 0.025% CDA were found to be optimal which is equivalent to 90–135 μl of CDA. Maximum light output was stable for up to 3 ½ minutes using 2–3 drops of 0.05% to 0.025% CDA. One drop was not enough and four drops were too much.

Example 7

20 μl aliquots of an *E. coli* culture were placed in either a 35 mm or a 100 mm petri dish, spread with a loop to cover the entire surface, and then allowed to dry. The ATP was extracted by placing 2 or 3 drops of 0.1, 0.05, 0.025, or 0.0125% CDA in the dish and swabbing it over the entire surface for 60 seconds. The swab was then placed in a counting tube with 20 μl of luciferase/luciferin reagent, and RLU were measured every 30 seconds for 120 seconds. As expected, lower RLU values were obtained when the *E. coli* was spread out over a larger surface area in the 100 mm petri dish. Optimal results for maximum light output and stability of light output were obtained with 2–3 drops of 0.05% CDA.

Example 8

Two types of counting tubes (5.6 mm diameter and 3.7 mm diameter) were prepared with 25 μl of 1× luciferase/ luciferin with 2.5% BSA. The tubes were dried in the refrigerator for three days, then placed in the lyophilizer at 4° C. for 1 hour. They were then tested by the addition of 125 μl of ATP prepared with 2% BSA, picked with a swab and twisted into the tube. The tubes were counted at 30 second intervals after waiting 1 min.

| 5.6 mm diameter results (RLU/s): | | | 3.7 mm diameter results (RLU/s): | | |
|---|---|---|---|---|---|
| 32678 | 34949 | 26467 | 16923 | 20448 | 28522 |
| 35981 | 37416 | 29273 | 21682 | 25558 | 33623 |
| 37933 | 38724 | 30451 | 28294 | 29288 | 36916 |
| 38402 | 39252 | 31222 | 28778 | 31452 | 38161 |
| 28387 | 39119 | 31854 | 30679 | 33364 | 38521 |

Higher counts (RLU/s) were obtained with the 5.6 mm inside diameter tube.

Example 9

E. coli were placed in separate 10×55 mm sterile polystyrene tubes in 20 μl aliquots. Three drops (ca 125 μl) of 0.05% CDA were added to each tube to extract bacterial ATP. After about 60 seconds, the extracted ATP sample from one tube was transferred with a pipet to a counting tube containing 50 μl of liquid luciferase/luciferin (liquid Z-Lux) reagent and then measured in a luminometer for 5 minutes at 30 second intervals. The extracted ATP sample from the other tube was absorbed into the tip of a sterile plain swab and then measured using a counting tube containing dried, immobilized luciferase/luciferin (Z-Lux tubes). Stable kinetics were obtained using the swab and immobilized luciferase/luciferin counting tube of the present invention but not with the liquid sample and liquid luciferase/luciferin.

It will be apparent to those skilled in the art that various modifications and variations can be made in the compositions and methods of the present invention without departing from the spirit or scope of the invention. Thus, it is intended that the present invention cover the modifications and variations of this invention provided they come within the scope of the appended claims and their equivalents.

What is claimed is:

1. A counting tube used in the rapid detection of ATP comprising:

a tube that fits in the sample compartment of a luminometer, and dried luciferase/luciferin reagent lining the inside of the tube, wherein the luciferase/luciferin reagent is prepared by placing about 10 to 50 μl of luciferase/luciferin reagent solution having a concentration of about 100 to 1,000 ng of luciferase and about 5 to 75 μg of luciferin into the tube, and drying the luciferase/luciferin reagent.

2. The counting tube of claim 1 wherein the luciferase/luciferin reagent is dried by refrigerating, lyophilizing, or both.

3. The counting tube of claim 1 wherein the luciferase/luciferin reagent is dried by refrigeration and then freeze-dried at 4° C. for about 30–120 minutes.

4. The counting tube of claim 1 wherein the bottom portion of the tube is conical and at the bottom has an inside diameter of about 4 to 6 mm.

5. The counting tube of claim 1 wherein the luciferase/luciferin reagent comprises about 375 ng of luciferase and about 25 μg of luciferin.

* * * * *